United States Patent [19]

Castensson et al.

[11] Patent Number: 5,567,677
[45] Date of Patent: Oct. 22, 1996

[54] PROTEIN FORMULATION COMPRISING GROWTH HORMONE

[75] Inventors: Staffan Castensson, Knivsta; Ebba Florin-Robertsson, Stockholm; Elvy Hokby, Enskede; Sirkka Thomé, Stockholm, all of Sweden

[73] Assignee: Pharmacia AB, Sweden

[21] Appl. No.: 162,017

[22] PCT Filed: Apr. 1, 1993

[86] PCT No.: PCT/SE93/00281

§ 371 Date: Dec. 20, 1993

§ 102(e) Date: Dec. 20, 1993

[87] PCT Pub. No.: WO93/19776

PCT Pub. Date: Oct. 14, 1993

[30] Foreign Application Priority Data

Apr. 3, 1992 [SE] Sweden .................................. 9201073

[51] Int. Cl.⁶ .................................. A61K 38/27
[52] U.S. Cl. .................. 514/12; 514/21; 530/399
[58] Field of Search .................. 530/399; 514/12, 514/21

[56] References Cited

U.S. PATENT DOCUMENTS

| | | | |
|---|---|---|---|
| 4,783,441 | 11/1988 | Thurow | 514/3 |
| 4,816,568 | 3/1989 | Hamilton, Jr. et al. | 530/399 |
| 4,917,685 | 4/1990 | Viswanathan et al. | 604/891.1 |
| 4,963,529 | 10/1990 | Fujioka et al. | 514/12 |
| 5,008,244 | 4/1991 | Miller et al. | 514/12 |
| 5,021,241 | 6/1991 | Yamahira et al. | 424/426 |
| 5,096,885 | 3/1992 | Pearlman et al. | 514/12 |

FOREIGN PATENT DOCUMENTS

| | | |
|---|---|---|
| 3077189 | 9/1989 | Australia . |
| 0211601 | 2/1987 | European Pat. Off. . |
| 0303746 | 2/1989 | European Pat. Off. . |
| 0406856 | 1/1991 | European Pat. Off. . |
| 0433113 | 6/1991 | European Pat. Off. . |
| 1-308235 | 12/1989 | Japan . |
| WO91/15509 | 10/1991 | WIPO . |
| WO91/18621 | 12/1991 | WIPO . |
| WO92/17200 | 10/1992 | WIPO . |
| WO93/22335 | 11/1993 | WIPO . |
| WO94/03198 | 2/1994 | WIPO . |

OTHER PUBLICATIONS

The U.S. Pharmacopeia, 21st Edition, 1985, pp. 1491–1493.
Skottner et al., Endocrinology, vol 124(5), 1989, pp. 2519–2526.
Chemical Abstract, vol. 113 (1990) pp. 374, Item 12165x.
The Merch Index, Eleventh Edition, 1989, pp. 1373–1374.

Primary Examiner—Chhaya D. Sayala
Attorney, Agent, or Firm—Pollock, Vande Sande & Priddy

[57] ABSTRACT

The invention relates to injectable formulations of growth hormone comprising citrate as buffer substance. The formulation could be an aqueous solution of growth hormone and citrate as buffer substance in a concentration of 2–50 mM. The formulation of the growth hormone could comprise growth factor, amino acids such as e.g. glycine and alanine and/or mannitol or other sugar alcohols and/or glycerol and/or other carbohydrates and optionally a preservative such as benzyl alcohol. The invention also relates to a process for preparation of the formulation by mixing growth hormone with citrate as buffer substance or by adding the constituents of the final formulation on the last gel purification step.

28 Claims, No Drawings

PROTEIN FORMULATION COMPRISING GROWTH HORMONE

The present invention relates to formulation of growth hormone or any functional analogue thereof, especially human growth hormone (hGH) in solutions, which comprise citrate in a concentration of about 2 to 50 mM as buffer substance and especially sodium citrate in an concentration of about 2 to 20 mM. This buffer is used for improving stability.

Growth hormone can be both human and animal such as human growth hormone (hGH), bovine growth hormone (bGH) and porcine growth hormone (pGH).

hGH is a protein Consisting of a single chain of 191 amino acids. The molecule is cross-linked by two disulphide bridges and the monomeric form has a molecular weight of 22 kDa. However, pituitary human growth hormone is not homogeneous. For example, a smaller 20 kDa hGH variant produced from the same gene is also known. The "basic hGH" variant (hGH-V) expressed by the placenta during pregnancy is another analogue which is a product of a separate gene. Like the 22 kDa hGH it consists of 191 amino acids but in various positions throughout the molecule 13 of them are different. See e.g. Bewley T. A. et al; Adv Enzymol; 42; 73–166; 1975 and Frankenne F. et al; J Ciin. Endocrin and Metabol; 66; 1171–80; 1988.

Recombinant hGH (22 kDa) has been commercially available for several years. It is preferred over the pituitary derived products because the product prepared from human tissue might contain infectious agents Such as that for the Creutzfeld-Jacob's disease. Two types of therapeutically useful recombinant hGH preparations are present on the market: the authentic one, e.g. Genotropin®, Kabi Pharmacia AB, and an analogue with an additional methionine residue at the N-terminal end, e.g. Somatonorm®.

hGH is used to stimulate linear growth in patients with hypo pituitary dwarfism or Turner's syndrome but other indications have also been suggested.

The stability of proteins in aqueous formulations is generally a problem in pharmaceutical industry.

It has often been solved by drying of the protein in different drying processes, such as freeze-drying. The protein has thereafter been distributed and stored in dried form. The patient necessarily has to reconstitute the dried protein in a solvent before use, which of course is a disadvantage and is an inconvenience for the patient.

By new devices for administrations, e.g. Kabipen® which is described in U.S. Pat. No. 4,968,299, Kabi Pharmacia AB, the patient has got a device which is rather simple to handle. The device comprises a two-chamber ampoule Genomix® containing hGH as a lyophilised powder in one of the compartments and a reconstitution diluent in the other. The patient reconstitutes the product before use. The lyophilised product can be stored for up to 24-months. The reconstituted product is then stable for 3 weeks when stored at 2°–8° C.

The freeze-drying process is a costly and time consuming process step, and it would be of great advantage if this step could be avoided, when preparing a commercial product of a protein.

For a patient, who needs daily injections of a growth hormone e.g. hGH, and especially when the patient is a child, it is of importance that the product is easy to handle, to dose and inject. The reconstitution of freeze-dried hGH demands prudence and carefulness and should preferably be avoided, but is the only method available today.

It would facilitate the use of growth hormone and especially hGH, if the protein could be produced and distributed as a solution to the patient, who could inject the medicament directly without reconstitution.

Different solutions to this problem have been disclosed, but until now no product has appeared on the market.

In WO 89/09614, Genentech, a stabilised formulation of hGH comprising glycine, mannitol and a buffer is disclosed and in a preferred embodiment a non-ionic surfactant such as polysorbate 80 is added. Sodium-phosphate is suggested as buffer substance. The formulation has an increased stability in a lyophilised formulation and upon reconstitution.

Another possibility of administering growth hormone in a solution is to add a block copolymer containing polyoxyethylene-polyoxypropylene according to EP 211 601, International Minerals and Chemical Corporation. This solution provides for a prolonged release upon administration to the animal.

There is a demand on the market for stabilised, injectable growth hormone solutions, e.g. hGH in a solution. It would also be advantageous if the final pharmaceutical solution only contained a minimum of additives, such as tensides.

We have now found a new formulation which solves the above mentioned problems.

GH STABILITY

The stability of hGH depends on the chemical and physical properties of the protein.

Different degradation pathways are known such as deamidation, oxidation and aggregation.

Deamidation and oxidation are common chemical reactions comprising changes of the primary structure of the protein. Deamidation occurs especially in aqueous solutions but low temperature and low pH of the solutions suppress the deamidation reaction.

Different forms of aggregation result from the physical instability of the protein. Aggregates can be soluble or insoluble and binding of both the forms Can be covalent or non covalent.

The aggregates can give opalescent solutions but there can also be non-visible aggregation which only can be shown chemically.

The prevention of covalent aggregation in protein formulations is of importance since such processes are irreversible and could result in the production of inactive species which in addition also may be immunogenic.

Changes in the primary structure may also give rise to conformational changes which can be the cause of self association of the protein, aggregation.

The non covalent aggregation occurring under certain conditions can lead to precipitation and loss of activity.

A large number of reactions can occur under different pH conditions and it is almost impossible to formulate a protein at a particular pH that eliminates all the modification reactions while maintaining high solubility and proper conformation of the protein.

Until now a slightly alkaline pH has generally been used by manufacturers to avoid visible particles and to obtain a clear product. In most commercial products the pH is over 7, in spite of the higher risk for deamidation.

When Kabi Pharmacia's product Genotropin® is reconstituted, a pH of 6.7 is obtained at a hGH concentration of 16 IU/ml. This pH is a compromise between a pH giving a totally clear solution (pH 8) and pH 6 giving a lower deamidation rate but somewhat more opalescence.

Because of this complexity it is not possible to formulate a protein preparation and eliminate all the degradation pathways. The freeze-dried protein product is much more stable than the corresponding aqueous solution. However, although a freeze-dried product is sufficiently stable after processing, the protein will still degrade slowly during storage.

THE INVENTION

Totally unexpected we have now found that solutions containing growth hormone in which citrate has been chosen as a buffer substance are more stable than those in which phosphate is the buffer.

The invention relates to injectable formulations of growth hormone or any functional analogue thereof, comprising citrate as buffer substance.

The formulation could be an aqueous solution of growth hormone or any functional analogue thereof and citrate as buffer substance in a concentration of 2–50 mM and preferably contains sodium citrate as buffer substance in a concentration of 2–40 mM at a pH of about 5.0 to 7.5.

Preferably the formulation is an aqueous solution of hGH or any functional analogue thereof and citrate as buffer substance in a concentration of 2 to 20 mM, e.g. 5 mM or 10 mM and preferably contains sodium citrate as buffer substance at a pH of about 6.0 to 7.0.

The formulation of the growth hormone or any functional analogue thereof could comprise amino acids such as e.g. glycine and alanine and/or mannitol or other sugar alcohols and/or glycerol and/or other carbohydrates and optionally a preservative such as benzyl alcohol. The solution should be isotonic. The growth hormone is preferably recombinant hGH.

The formulation according to the invention is stable for at least 12 months. By stable is here meant an amount of more than 85% monomer (IEF) and fragments according to SDS-PAGE of less than 2%.

The claimed formulation can also comprise growth hormone and growth factors in a mixture.

By growth factor is meant insulin-like growth factors (IGF-1 or IGF-2 and epidermal growth factor (EGF), either from natural sources or produced by recombinant techniques.

The invention also relates to a process for preparation of the formulation by mixing growth hormone or any functional analogue thereof with citrate as buffer substance or by adding the constituents of the final formulation on the last gel purification step.

It also relates to a method for treatment of a patient in need of growth hormone any functional analogue thereof by administering the claimed formulation.

By growth hormone (GH) is meant both naturally occurring human and animal GH and recombinant GH (rGH), such as rhGH, rbGH and rpGH. By functional analogues are meant compounds having the same therapeutic effect as the growth hormone in animals and humans.

The growth hormone to be included in the buffer could be the initially isolated product or a product which has been freeze-dried and thereafter reconstituted.

The concentration of the growth hormone is only dependent of its solubility in the used buffer and the desired therapeutically amount for the given dose, Preferably the concentration of hGH is 1–80 IU/ml and more preferably 2–40 IU/ml.

Aggregation in the form of precipitation observed by shaking the solution, is a result of denaturation at the air-liquid interface. This could be avoided by filling without headspace, thus diminishing the condition for aggregation.

EXAMPLE 1

Material for formulation studies was obtained from the ordinary Genotropin® process. The human growth hormone is synthesized in the bacterium *Escherichia coli* (*E. coli*) K12, using the expression plasmid pAPSTIIhGH-3 as template. The hormone is secreted out from the cell into the periplasmatic space during synthesis. Human growth hormone is subsequently isolated from the *E. coil* periplasmic space after disruption of the outer bacterial membrane.

The extract containing recombinant hGH was fractionated on DEAE-Sepharose FF. Two ammonium sulphate precipitation steps followed and thereafter two fractionation steps on DEAE-Sepharose FF. Formulation was performed by gel filtration which serves the purposes of removing salts used in the previous purification steps and adding the constituents of the final formulation. The last column Sephadex G-25 (Pharmacia, diameter 1.3 cm, bed height 45 cm) was equilibrated with the formulation buffer. Equilibration and chromatography was performed at +7° C.

The desired protein concentration was achieved by diluting with the formulation buffer.

The stability of seven solutions was investigated. Se table 1.

TABLE 1

| Example | A | B | C | D |
|---|---|---|---|---|
| hGH IU/ml | 20 | 20 | 10 | 10 |
| Na-citrate, mM | 5 | — | — | — |
| Na-phosphate, mM | — | 5 | 10 | 10 |
| glycine, mM | 12 | 12 | 12 | 12 |
| mannitol, mM | 250 | 250 | 250 | 250 |
| pH | 6, 2 | 6, 3 | 6, 2 | 7, 4 |
| Volume | 1 | 1 | 1 | 1 |
| Starting values: | | | | |
| pH | 6, 2 | 6, 3 | 6, 2 | 7, 4 |
| IEF (% monomer) | 98 | 98 | 99 | 100 |
| SDS-PAGE | | | | |
| aggregates, % | 0 | 0 | — | — |
| monomer, % | 99, 8 | 99.6 | — | — |
| fragments, % | 0, 2 | 0.4 | — | — |
| visual inspect. | clear | clear | clear | clear |

| Example | A | B |
|---|---|---|
| The results after 6 months' storage at 5° C.: | | |
| pH | 6, 3 | 6, 4 | 6, 4 | 7, 5 |
| IEF (% monomer) | 88 | 84 | 88 | 73 |
| SDS-PAGE | | |
| aggregates, % | 0 | 0 | 0 | 0, 2 |
| monomer, % | 99, 7 | 95, 1 | 97, 5 | 98, 4 |
| fragments, % | 0, 3 | 4, 9 | 2, 5 | 1, 3 |
| visual inspect. | clear | — |
| The results after 15 months' storage at 5° C.: | | |
| pH | 6, 3 | 6, 4 |
| IEF (% monomer) | 86 | 75 |
| SDS-PAGE | | |
| aggregates, % | 0 | 0, 1 |
| monomer, % | 98, 9 | 92, 7 |
| fragments, % | 1, 0 | 7, 3 |
| visual inspect. | clear | clear |
| The results after 24 months' storage at 5° C.: | | |
| pH | 6, 4 | 6, 4 |
| IEF (% monomer) | 88 | 71 |
| SDS-PAGE | | |
| aggregates, % | 0 | 0 |
| monomer, % | 98, 3 | 89, 1 |
| fragments, % | 1, 7 | 10.9 |
| visual inspect. | clear | clear |

TABLE 2

| Example | E | F | G | H |
|---|---|---|---|---|
| hGH IU/ml | 4 | 4 | 10 | 10 |
| Na-citrate, mM | 10 | — | — | 5 |
| Na-phosphate, mM | — | 10 | 10 | — |
| glycine, mM | 12 | 12 | 12 | 12 |
| mannitol, mM | 250 | 250 | 250 | 250 |
| pH | 6, 2 | 6, 1 | 6, 3 | 6, 1 |
| Volume | 3 | 3 | 2 | 0.35 |
| Starting values: | | | | |
| pH | 6, 2 | 6, 1 | 6, 3 | 6.1 |
| IEF (% monomer) | 99 | 99 | 97 | 100 |
| visual inspect. | clear | clear | clear | clear |
| The results after 6 months' storage at 5° C.: | | | | |
| pH | 6, 3 | 6, 2 | 6, 3 | 6.6 |
| IEF (% monomer) | 89 | 86 | 85 | 91 |
| SDS-PAGE | | | | |
| aggregates, % | 0 | 0 | 0.1 | 0 |
| monomer, % | 99.8 | 97.1 | 95.2 | 98.1 |
| fragments, % | 0.2 | 2.9 | 4.7 | 1.9 |
| visual inspect. | clear | clear | clear | clear |
| The results after 12 months' storage at 5° C.: | | | | |
| pH | | | 6, 3 | 6.5 |
| IEF (% monomer) | | | 71 | 90 |
| SDS-PAGE | | | | |
| aggregate, % | | | 0, 4 | 0 |
| monomer, % | | | 93 | 98.1 |
| fragments, % | | | 6.6 | 1.8 |
| visual inspect. | | | — | clear |

METHODS

Isoelectric Focusing (IEF) with Densitometric Evaluation

IEF is a method according to which the extent of deamidation can be evaluated.

The separation of hGH components is carried out in a pH gradient, which is established between two electrodes and stabilised by carrier ampholytes. The proteins migrate until they align themselves at their isoelectric point in the gradient, at which a protein possesses no net overall charge and will therefore concentrate as migration ceases. Thus the separation is obtained according to charge. The relative distribution of charged hGH forms are quantified by densitometric scanning of Coomassie Blue stained polypeptides. The higher percentage of the monomer, the less deamidation.

Polypeptides Size Distribution (SDS-PAGE)

Proteins in preparations of somatropin, hGH, were denatured by sodium dodecyl sulphate (SDS) to yield negatively charged molecular complexes of SDS-protein. Separation was then obtained according to molecular size by electrophoresis in polyacrylamide gels (PAGE) in the presence of SDS. The relative polypeptide size distribution of hGH was quantified by desitometric scanning of the silver stained polypeptide bands.

Visual Inspection

The appearance of the solutions were eye-inspected according to Ph. Eur. 2nd Ed.

pH pH was measured with glass and calomel electrodes.

Examples A, E and H are according to the invention.

From tables 1 and 2 it is clearly seen that the percentage of fragment is much higher in the solution buffered with Na-phosphate than with Na-citrate.

B (Na-phosphate) contains after 15 months' storage at 5° C. 7.3% fragments and 92.7% of the monomer and A (Na-citrate) has 1.0% and 98.9% respectively.

For F (Na-phosphate) the relative amount of fragment is 2.9% and the percentage of monomer is 97.1% after 6 months' storage at 5° C. E (Na-citrate) has 0.2% and 99.8%, respectively.

B, C, D, F and G contain Na-phosphate and all have high percentage of fragments after storage.

D has a higher pH, but the amount of fragments is higher than for the solution E using 10 mM Na-citrate buffer.

The grade of deamidation is unacceptably high in D.

EXAMPLE 2

This example was performed in order to compare compositions according to the invention with and without benzyl alcohol. See table 3

The formulations were prepared in the same way as explained in example 1, but the formulation buffer solution contained bensyl alcohol.

TABLE 3

| Example | I | K | L | A |
|---|---|---|---|---|
| hGH IU/ml | 20 | 20 | 20 | 20 |
| Na-citrate, mM | 10 | 10 | 5 | 5 |
| glycine, mM | 12 | — | 12 | 12 |
| mannitol, mM | 150 | 150 | 130 | 250 |
| benzyl alcohol % | 1 | 1 | 1 | — |
| pH | 6.3 | 6.3 | 6.3 | 6.2 |
| Volume | 1 | 3.5 | 1 | |
| The result after 3 weeks' storage at 30° C.: | | | | |
| pH | 6.3 | 6.3 | 6.2 | 6.2 |
| IEF (% monomer) | 67 | 68 | 64 | 72 |
| clarity | clear | clear | clear | clear |
| The result after 1 month's storage at 5° C.: | | | | |
| pH | 6.3 | 6.3 | 6.2 | 6.2 |
| IEF (% monomer) | 99 | 99 | — | 97 |
| clarity | clear | clear | clear | clear |
| The results after 3 months' storage at 5° C. | | | | |
| pH | 6.3 | 6.4 | 6.2 | 6.3 |
| IEF (% monomer) | 94 | 94 | 96 | 94 |
| clarity | clear | clear | clear | clear |
| SDS-PAGE) | | | | |
| aggregates, % | | | 0 | 0, 1 |

EXAMPLE 2

This example was performed in order to compare compositions according to the invention with and without benzyl alcohol. See table 3

The formulations were prepared in the same way as explained in example 1, but the formulation buffer solution contained bensyl alcohol.

TABLE 3

| Example | I | K | L | A |
|---|---|---|---|---|
| hGH IU/ml | 20 | 20 | 20 | 20 |
| Na-citrate, mM | 10 | 10 | 5 | 5 |
| glycine, mM | 12 | — | 12 | 12 |
| mannitol, mM | 150 | 150 | 130 | 250 |
| benzyl alcohol % | 1 | 1 | 1 | — |
| pH | 6.3 | 6.3 | 6.3 | 6.2 |
| Volume | 1 | 1 | 3.5 | 1 |
| The result after 3 weeks' storage at 30° C.: | | | | |
| pH | 6.3 | 6.3 | 6.2 | 6.2 |
| IEF (% monomer) | 67 | 68 | 64 | 72 |
| clarity | clear | clear | clear | clear |
| The result after 1 month's storage at 5° C.: | | | | |
| pH | 6.3 | 6.3 | 6.2 | 6.2 |
| IEF (% monomer) | 99 | 99 | — | 97 |
| clarity | clear | clear | clear | clear |
| The results after 3 months' storage at 5° C. | | | | |
| pH | 6.3 | 6.4 | 6.2 | 6.3 |
| IEF (% monomer) | 94 | 94 | 96 | 94 |
| clarity | clear | clear | clear | clear |
| SDS-PAGE) | | | | |
| aggregates, % | | | 0 | 0, 1 |
| monomer, % | | | 99.8 | 99.4 |
| fragments, % | | | 0.2 | 0.5 |

Example 2 is performed to show how the addition of benzyl alcohol influences stability when Na-citrate is used as buffer.

Benzyl alcohol is a preservative which is conditional to use in injectable multidose preparations.

According to the pharmacopoeias it is a demand that a suitable preservative is added to injectable multidose preparations in order to guarantee the microbial safety of the product.

As benzyl alcohol has an influence on the isotonicity the amount of mannitol is adjusted accordingly when benzyl alcohol is added.

From Table 3 it is clearly seen that the addition of benzyl alcohol has no influence on stability when Na-citrate is used as buffer.

EXAMPLE 3

This example was performed in order to compare compositions according to the invention with and without glycine and mannitol. See table 4

The formulations were prepared in the same way as explained in example 1.

TABLE 4

| Example | M | N |
|---|---|---|
| hGH IU/ml | 20 | 20 |
| Na-citrate, mM | 5 | 5 |
| glycine, mM | — | 12 |
| mannitol, mM | — | 150 |
| pH | 6.3 | 6.3 |
| Volume | 1 | 1 |
| The result after 1 weeks' storage at 30° C: | | |
| pH | 6.3 | 6.3 |
| IEF (% monomer) | 92 | 91 |
| SDS-PAGE) | | |
| aggregates, % | 0 | 0 |
| monomer, % | 99.5 | 99.6 |
| fragments, % | 0.5 | 0.4 |
| visual inspect. | clear | clear |

From Table 4 it is seen that the addition of additives such as glycine and mannitol has no influence on stability when Na-citrate is used as buffer.

We claim:

1. A stabilized injectable growth hormone formulation being stable for at least 12 months, consisting of a solution of human growth hormone (hGH) as the growth hormone in said formulation and citrate in an amount of 2–50 mM as buffer substance at a pH of about 5.0 to 7.0 to thereby stabilize said growth hormone in said formulation.

2. Formulation according to claim 1 in which the formulation is an aqueous solution of said human growth hormone.

3. Formulation of growth hormone according to claim 2 in which hGH is recombinant hGH.

4. Formulation according to claim 2 in which the formulation is an aqueous solution of hGH and citrate as buffer substance in concentration of 2 to 20 mM.

5. Aqueous solution of hGH according to claim 2, wherein the citrate used as a buffer substance is sodium citrate and the pH ranges between about 6 and 7.

6. Aqueous solution of hGH according to claim 4, wherein the citrate used as a buffer substance is sodium citrate and the pH ranges between about 6 and 7.

7. Formulation of hGH according to claim 1, wherein the citrate used as a buffer substance is sodium citrate and the pH ranges between about 6 and 7.

8. Formulation of hGH according to claim 7, wherein the citrate used is sodium citrate in an amount of 5 mM.

9. Formulation of hGH according to claim 7, wherein the citrate used is sodium citrate in an amount of 10 mM.

10. Process for preparation of a formulation according to claim 1, comprising mixing said human growth hormone with citrate as buffer substance in a gel purification step.

11. Method for treatment of a patient in need of growth hormone by administering a formulation according to claim 1.

12. A stabilized injectable growth hormone formulation being stable for at least 12 months, consisting of a solution of human growth hormone as the growth hormone in said formulation, citrate in an amount of 2–50 mM as buffer substance at a pH of about 5.0 to 7.0 to thereby stabilize said growth hormone in said formulation and a member selected from the group consisting of amino acids, sugar alcohol, glycerol, carbohydrates, preservative, and mixtures thereof.

13. Formulation according to claim 12 in which the formulation is an aqueous solution of said human growth hormone.

14. Formulation of growth hormone according to claim 13 in which hGH is recombinant hGH.

15. Aqueous solution of hGH according to claim 13, wherein the citrate used as a buffer substance is sodium citrate and the pH ranges between about 6 and 7.

16. Formulation of growth hormone according to claim 13, wherein said member is selected from the group consisting of glycine, mannitol, glycerol and mixtures thereof.

17. Formulation of growth hormone according to claim 13, wherein said member includes a preservative.

18. Formulation according to claim 13 in which the formulation is an aqueous solution of hGH and citrate as buffer substance in concentration of 2 to 20 mM.

19. Aqueous solution of hGH according to claim 18, wherein the citrate used as a buffer substance is sodium citrate and the pH ranges between about 6 and 7.

20. Formulation of growth hormone according to claim 18, wherein said member includes a preservative.

21. Formulation of hGH according to claim 12, wherein the citrate used as a buffer substance is sodium citrate and the pH ranges between about 6 and 7.

22. Formulation of hGH according to claim 21, wherein the citrate used is sodium citrate in an amount of 5 mM.

23. Formulation of hGH according to claim 21, wherein the citrate used is sodium citrate in an amount of 10 mM.

24. Formulation of growth hormone according to claim 12, wherein said member is selected from the group consisting of glycine, mannitol, glycerol and mixtures thereof.

25. Process for preparation of a formulation according to claim 12, comprising mixing said human growth hormone with citrate as buffer substance and said member in a gel purification step.

26. Method for treatment of a patient in need of growth hormone by administering a formulation according to claim 12.

27. Formulation of growth hormone according to claim 12, wherein said member includes a preservative.

28. Formulation of growth hormone according to claim 27 which is an aqueous solution of hGH and the preservative is benzyl alcohol.

* * * * *